United States Patent [19]

Fabry et al.

[11] Patent Number: 4,943,393
[45] Date of Patent: Jul. 24, 1990

[54] PROCESS FOR THE MANUFACTURE OF ESTER SULFONATE PASTES OF LOW VISCOSITY

[75] Inventors: Bernd Fabry, Korschenbroich; Robert Piorr, Ratingen-Hoesel, both of Fed. Rep. of Germany

[73] Assignee: Henkel Kommanditgesellschaft auf Aktien, Duesseldorf-Holthausen, Fed. Rep. of Germany

[21] Appl. No.: 310,274

[22] Filed: Feb. 13, 1989

[30] Foreign Application Priority Data

Feb. 13, 1988 [DE] Fed. Rep. of Germany ....... 3804609

[51] Int. Cl.$^5$ ................................................ C11D 1/28
[52] U.S. Cl. ...................................... 252/554; 252/353; 252/557; 252/DIG. 14
[58] Field of Search ............... 252/535, 538, 554, 557, 252/DIG. 14

[56] References Cited

U.S. PATENT DOCUMENTS

| | | | |
|---|---|---|---|
| 3,345,301 | 10/1967 | Stein et al. | 252/554 |
| 3,729,431 | 4/1973 | Smitherman | 252/535 |
| 4,495,092 | 6/1985 | Schmid et al. | 252/559 |
| 4,532,076 | 7/1985 | Schmid et al. | 252/557 |
| 4,547,318 | 10/1985 | Kloetzer et al. | 260/400 |
| 4,675,128 | 6/1987 | Linde et al. | 252/559 |
| 4,772,426 | 9/1988 | Koch et al. | 252/549 |
| 4,820,451 | 11/1989 | Piorr et al. | 260/400 |
| 4,865,774 | 12/1989 | Fabry et al. | 252/554 |

FOREIGN PATENT DOCUMENTS

| | | |
|---|---|---|
| 0186896 | 7/1986 | European Pat. Off. . |
| 0222237 | 5/1987 | European Pat. Off. . |
| 1418887 | 5/1971 | Fed. Rep. of Germany . |
| 3319591 | 12/1984 | Fed. Rep. of Germany . |
| 3538910 | 5/1987 | Fed. Rep. of Germany . |
| 1001285 | 8/1965 | United Kingdom . |
| 1066764 | 4/1967 | United Kingdom . |

*Primary Examiner*—Prince E. Willis
*Attorney, Agent, or Firm*—Ernest G. Szoke; Wayne C. Jaeschke; John E. Drach

[57] ABSTRACT

Compounds of the formula

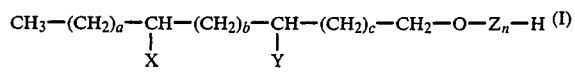

$$CH_3-(CH_2)_a-\underset{X}{CH}-(CH_2)_b-\underset{Y}{CH}-(CH_2)_c-CH_2-O-Z_n-H \quad (I)$$

wherein X and Y are different and are OH or SO$_3$M wherein M is selected from the group consisting of hydrogen, an alkali metal ion, an alkaline earth metal ion, NR$_4$ wherein R is hydrogen, an alkyl or hydroxy alkyl radical having from 1 to 4 carbon atoms; a and c are integers having a value of from 0 to 18; b is an integer having a value of from 0 to 2 such that the sum of a+b+c is from 12 to 18; Z is an oxyethylene, oxypropylene, or oxybutylene group; n is an integer having a value of from 0 to 30 reduce the viscosity of highly concentrated, aqueous pastes of alkali metal salts of α-sulfonated fatty acid alkyl esters by as much as 90% of their original value.

11 Claims, No Drawings

PROCESS FOR THE MANUFACTURE OF ESTER SULFONATE PASTES OF LOW VISCOSITY

BACKGROUND OF THE INVENTION

1. Field of the Invention:

The invention relates to a process for the manufacture of low-viscosity highly concentrated aqueous pastes of alkali metal salts of of α-sulfonated fatty acid alkyl esters.

2. Description of the Related Art:

Alkali metal salts of α-sulfo fatty acid alkyl esters are known to be obtained in the form of aqueous pastes by the neutralization of α-sulfo fatty acid esters with aqueous alkali metal hydroxide. As the industrial starting material, renewable raw materials of natural origin, are increasingly being used, mainly fats and/or oils of vegetable origin, from which the fatty acid alkyl esters are obtained either by ester splitting and subsequent esterification with low alkanols, particularly methanol, or by the transesterification of natural triglycerides with low alkanols. The fatty acid ester mixtures that result—depending on the origin of the natural raw material—contain esters of fatty acids of a comparatively wide carbon number range, which is normally between 10 and 24 for the fatty acid radical. Fatty acid ester mixtures of this type are preferably sulfated with gaseous sulfur trioxide. This results in more or less strongly colored acidic crude sulfonates, which are bleached and converted into ester sulfonate pastes by neutralization to the pH-range of around 6 to 7. In this form they are very important as surface-active agents or wetting agents for washing and cleaning purposes.

A particular difficulty experienced in the industrial handling of these pastes of alkali metal salts of α-sulfonated fatty acid alkyl esters—known in the following as "ester sulfonate salts"—lies in their concentration/viscosity characteristics. Industrially occurring ester sulfonate salts only form sufficiently mobile, e.g. that can be pumped, solutions or suspension in aqueous admixture, with the low viscosity to still ensure the problem-free running of industrial processes, when they have comparatively low solid concentrations, e.g. solid concentrations of up to about 35% by weight. With higher ester sulfonate salt contents, e.g. solid contents of around 40% by weight or more, the viscosity of the aqueous preparation increases so sharply that it no longer has free mobility. This causes serious limitations: the aim of producing highly concentrated ester sulfonate salt pastes directly by neutralization of the crude sulfonic acid mixture with a concentrated alkali metal hydroxide solution, cannot be achieved because the capacity to be stirred of the mixture and therefore the even mixing of the two components of the reaction mixture (crude sulfonic acid mixture and alkali metal hydroxide solution) is no longer ensured. At the same time therefore it becomes impossible for the neutralization heat to be carried away. Unwelcome secondary reactions occur due to local concentration and temperature peaks. It is disadvantageous apart from this that the ester sulfonate pastes immobilized by the viscosity increase are no longer pumpable in the industrial plant. The blockage of pipes occurs and with it a lasting disturbance of the operation of the entire plant.

The prior art on ester sulfonate salt pastes deals intensively with such peculiarities. To improve the flow behaviour and therefore the industrial ease of handling of this type of paste it has in particular been suggested that flow aids or viscosity regulators are added to the aqueous concentrates of α-sulfor fatty acid alkyl ester salts obtained on an industrial scale. For example, U.S Pat. No. 4,495,092 depicts the concomitant use of $C_8$ to $C_{40}$ alcohols, which can in addition have one or more hydroxyl groups as substituents and to which up to 20 mol of ethylene oxide and/or propylene oxide per mol of alcohol can be added. These viscosity regulators are added to the ester sulfonate pastes in quantities of 1 to 15% by weight in relation to the amount of ester sulfonate salt such that the viscosity of the ester sulfonate paste adjusts to a maximum of 10 000 mPa.s at 70° C. With a viscosity in this range one can also ensure that the mixture can be pumped.

U.S. Pat. No. 4,675,128 describes the use of alkali metal alkane sulfonates with an average carbon number of 11 to 21 as viscosity regulators for aqueous highly concentrated industrial α-sulfo-fatty-acid-ester alkali-metal-salt concentrates, which contain at least 30% by weight of the active ester sulfonate salt. The viscosity regulators are used in quantities of 0.5 to 10% by weight referred to the ester sulfonate salt content, and ensure a viscosity at 40° C. of a maximum of 10 000 mPa.s and therefore also pumpability of the ester sulfonate salt concentrates in the industrial field.

According to German Patent Application No. 35 38 910 mobile aqueous pastes of wash-active α-sulfo fatty acid ester salts can be manufactured from crude sulfonic acids at high temperatures by subjecting the crude sulfonic acids to a subsequent reaction with monovalent alcohols and/or their alkoxylation products before introduction into the aqueous alkali metal hydroxide phase. Preferably, monofunctional alkanols with up to 30 carbon atoms in the alcohol radical are used, or their alkoxylation products with up to 20 alkoxy radicals in the molecule. Also with this process one can obtain ester sulfonate salt pastes that are easily mobile precisely in the critical concentration range of around 35 to 60 % by weight, and which are also easy to process on an industrial scale.

The disadvantages of the solutions proposed by the prior art for the problem of reducing the viscosity of ester sulfonate salt pastes by the addition of alcohols, are to be seen in that the neutralized products of the process contain in high quantities the alcohol that has been added to set low viscosity values. This is undesirable because the short-chained alcohol interferes with the manufacture of detergent mixtures by spray-drying. In particular the undesirable "pluming" (aerosol formation during spray-drying) effect is caused by the presence of the alcohol additives. The free alcohols in the ester sulfonate salt mixture moreover also have an undesirable alien odor and deodorization of the product is therefore necessary. Before the spraying of the aqueous pastes for the manufacture of detergents, it may be necessary for this reason to interpose process stages to drive out the excess alcohol. This however increases the cost of the process as a whole in an undesirable way.

It is an object of the present invention, therefore, to provide a process for the manufacture of ester sulfonate salt pastes in which an improvement of the flow behaviour of the pastes at high active substance concentrations can be achieved. Compounds or mixtures of compounds should be used for the adjustment of the viscosity in this process which have a significant viscosity-reducing effect even in small concentrations. These substances should not however effect, or at least not disadvantageously effect, the properties of the product.

The solution to the problem consists in using compounds known as hydroxy ocenol sulfonates which have the formula

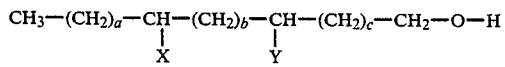

wherein X is SO$_3$M, Y is OH or X is OH, Y is SO$_3$M, and M is selected from the group consisting of hydrogen, an alkali metal ion, an alkaline earth metal ion, or NR$_4$ wherein R is hydrogen, an alkyl or hydroxy alkyl radical having from 1 to 4 carbon atoms; a and c are integers having a value of from 0 to 18, b is an integer having a value of from 0 to 2 such that the sum of a+b+c is from 12 to 18 alone or in combination with compounds known as hydroxy ocenol ether sulfonates which have the formula

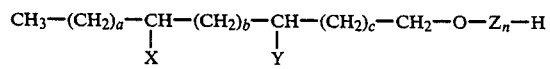

wherein X is SO$_3$M, Y is OH or X is OH, Y is SO$_3$M, and M selected from the group consisting of hydrogen, an alkali metal ion, an alkaline earth metal ion, NR$_4$ wherein R is hydrogen, an alkyl or hydroxy alkyl radical having from 1 to 4 carbon atoms; a and c are integers having a value of from 0 to 18, b is an integer having a value of from 0 to 2 such that the sum of a+b+c is from 12 to 18; Z is an oxyethylene, oxypropylene, or oxybutylene group; n is an integer having a value of from 1 to 30. The hydroxy ocenol sulfonates and/or hydroxy ocenol ether sulfonates are used in low concentrations in the manufacturing processes as substances for reducing the viscosity, and thus effecting a clear reduction in the viscosity of the aqueous ester sulfonate salt pastes with a high surface active-substance (sulfonate ester salts) content.

DESCRIPTION OF THE INVENTION

One aspect of the present invention relates to a process for the manufacture of highly concentrated, low-viscosity aqueous pastes of alkali metal salts of α-sulfonated fatty acid alkyl esters, which, with high solid contents are mobile even at moderately high temperatures with high solid contents comprising the steps of:

(a) sulfonating an alkyl fatty acid ester with a sulfonating agent to produce an α-sulfonated fatty acid alkyl ester;

(b) adding to said α-sulfonated fatty acid alkyl ester an amount of at least one compound of the formula

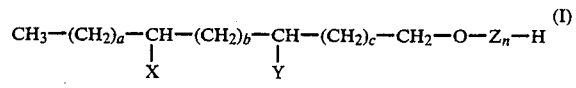

sufficient to reduce the viscosity of said α-sulfonated fatty acid alkyl ester to from about 10% to about 90% of its value before the addition of said compound of formula I; wherein in the compound of formula I X and Y are different and are OH or SO$_3$M wherein M is selected from the group consisting of hydrogen, an alkali metal ion, an alkaline earth metal ion, or NR$_4$ wherein R is hydrogen, an alkyl or hydroxy alkyl radical having from 1 to 4 carbon atoms; a and c are integers having a value of from 0 to 18; b is an integer having a value of from 0 to 2 such that the sum of a+b+c is from 12 to 18; Z is an oxyethylene, oxypropylene, or oxybutylene group; n is an integer having a value of from 0 to 30; and (c) neutralizing said α-sulfonated fatty acid alkyl ester with an aqueous alkaline solution.

Another aspect of the present invention relates to highly concentrated, low-viscosity aqueous pastes which, with high solid contents are mobile even at moderately high temperatures comprising alkali metal salts of α-sulfonated fatty acid alkyl esters and one or more compounds having the formula

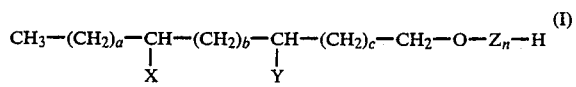

wherein X and Y are different and are OH or SO$_3$M wherein M is selected from the group consisting of hydrogen, an alkali metal ion, an alkaline earth metal ion, or NR$_4$ wherein R is hydrogen, an alkyl or hydroxy alkyl radical having from 1 to 4 carbon atoms; a and c are integers having a value of from 0 to 18, b is an integer having a value of from 0 to 2 such that the sum of a+b+c is from 12 to 18; Z is an oxyethylene, oxypropylene, or oxybutylene group; n is an integer having a value of from 0 to 30; said compound of formula I being present in such an amount that the viscosity of said composition is from about 10% to about 90% lower than the viscosity of said aqueous solution of a salt of an α-sulfonated fatty acid alkyl ester.

The process according to the invention for the manufacture of low-viscosity highly concentrated aqueous pastes of the alkali metal salts of α-sulfonated fatty acid alkyl esters follows, in several essential stages of the process, corresponding processes which are known from the prior art for the manufacture of such compounds. Fats and/or oils of natural origin serve today as the starting materials in the industrial sphere, from which the fatty acid alkyl esters can be manufactured economically in large quantities by ester splitting and a subsequent esterification with lower alkanols, preferably with methanol, or alternatively by the transesterification of ester radicals of triglycerides of natural origin with the corresponding lower alkanols. In preferred embodiments fats and/or oils of vegetable origin are used for this which have a range of chain lengths of the fatty acid radicals which is desirable for the manufacture of such compounds.

This range normally lies between 10 and 24 carbon atoms in the fatty acid alkyl radical. It is possible to use such fatty acid alkyl esters as pure compounds; in the field of industry however the fatty acid ester mixtures that result from industrial fat or oil production are frequently used as starting materials. The sulfonation of such fatty acid esters or fatty acid ester mixtures is carried out in the presence of a conventional sulfonation reagent. Preferably, gaseous SO$_3$ or mixtures with inert gases (air, nitrogen) are used, which contain relatively large quantities of SO$_3$. Alternatively, it is in addition also possible to use other sulfonation reagents for the sulfonation. Chlorsulfonic acid is given as an example. The sulfonation agent is normally used in molar excess. This means that per mol. of fatty acid alkyl ester 1.2 to 2 mol. of the sulfonation agent, preferably gaseous SO$_3$, is used. The sulfonation reaction is taken to relatively high degrees of sulfonation to attain the highest possible product yield. The aim is for degrees of sulfonation of the order of 95%. In the individual case of the sulfonation of particular fatty acid alkyl esters or fatty acid alkyl ester mixtures, the degree of sulfonation that can be obtained depends, however, on numerous individual factors. The first limiting factor is the dark coloration of the crude sulfonates that is frequently observed with high degrees of sulfonation, and which necessitates an additional bleaching stage in the later course of the process. A compromise should therefore be found in each individual case to ensure the optimum degree of sulfonation and light coloration of the product.

A further stage of the process to be provided depending on the color of the α-sulfo fatty acid ester obtained, is the bleaching of the crude sulfonates which is normally effected by the mixing of the crude product mixtures with hydrogen peroxide and/or aqueous hypochlorite solutions. Another subsequent bleaching may possibly also be necessary before or during the final storage of the already neutralized pastes. This process is also known to the expert from the prior art and therefore requires no further explanation here.

A stage of the process also known per se consists in the introduction of the if necessary already bleached crude sulfonates into aqueous alkali metal hydroxide solutions with the formation of salts. This stage of the process also results essentially from the publications known from the prior art and is effected in the preferred manner by the if necessary bleached crude sulfonates being introduced into an aqueous solution of an alkali metal hydroxide, and preferably into an aqueous solution of sodium hydroxide. To avoid peaks of concentration and temperature, the solution must be intensively mixed and cooled. Appropriate devices for the industrial operations are also known to the expert from the prior art and therefore require no further explanation.

According to the invention one or more hydroxy ocenol sulfonates and/or hydroxy ocenol ether sulfonates are added to the reaction mixture in the process for the manufacture of the aqueous ester sulfonate salt pastes. It is possible here to add individual compounds from the group of the hydroxy ocenol sulfonates or individual compounds from the group of the hydroxy ocenol ether sulfonates. Several compounds from one group can however also be used in combination with each other or also with one or more compounds from the other group. Corresponding to the method of manufacture of these compounds, which will be dealt with in more detail below, these usually occur in industrial processes in mixtures, the use of mixtures of such compounds in industrial processes is therefore also preferred for the manufacture of ester sulfonate pastes of low viscosity.

In a preferred embodiment of the invention one or more compounds of the formula (I)

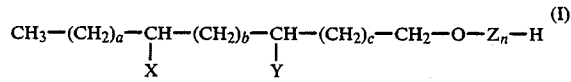

are added to the reaction mixture,

In this general formula (I), X and Y represent different substituents from each other, which stand for OH or SO$_3$M, in which M signifies hydrogen, an alkali metal, an alkaline earth metal or an ammonium radical. Such alkali metals are preferably lithium, sodium, or potassium, of which sodium is naturally particularly preferred. As alkaline earth metals magnesium, calcium, strontium or barium are possible, whereby one should consider that one alkaline earth metal ion links two molecules of the general formula (I) linked via SO$_3$ groups. The ammonium radical can be either NH$_4$ radicals or NR$_4$ radicals, in which R can represent either hydrogen or an alkyl radical or a hydroxy alkyl radical with 1 to 4 carbon atoms. In preferred embodiments of the process according to the invention those compounds of the general formula (I) are used, in which X or Y represent a SO$_3$M group, in which M signifies sodium or ammonium (NH$_4$)

In the general formula (I) Z stands for oxyethylene groups, oxypropylene groups or oxybutylene groups. Of these groups the oxyethylene radicals are preferred. n in the general formula (I) can stand either for 0, whereby the compounds of the general formula (I) in which n stands for 0, are hydroxy ocenol sulfonates, or for numbers in the range of 1 to 30, whereby such compounds are then hydroxy ocenol ether sulfonates. In the process according to the invention it is preferred to add those compounds of the general formula (I) in which n stands for numbers in the range of 0 to 10. This means that the preferably added compounds are either hydroxy sulfonates or hydroxy ocenol ether sulfonates, whereby the latter contain 1 to 10 ethoxy groups on the end of the molecule.

In the general formula (I) given above, a and c also stand for numbers in the range of 0 to 18 and b for 0, 1 or 2, such that the sum of (a+b+c) is in the range of the numbers from 12 to 18. Preferably such compounds of the general formula (I) are added in which the sum of (a+b+c) is 16 or 18. The corresponding hydroxy ocenol sulfonates or hydroxy ocenol ether sulfonates therefore derive from unsaturated fatty alcohols such as for example oleyl alcohol and linoleyl alcohol, which carry 16 to 18 carbon atoms in the alkenyl radical.

One or more hydroxy ocenol sulfonates and/or hydroxy ocenol ether sulfonates are added to the reaction mixture in the process according to the invention for the manufacture of α-sulfo fatty acid alkyl ester salts with low viscosity. It is possible here to add to the crude sulfonic acid one or more hydroxy ocenol sulfonates alone or in mixtures with one or more hydroxy ocenol sulfonates, before this is introduced into the aqueous basic solution. According to another embodiment of the process it is possible to add the hydroxy ocenol sulfonate(s) and/or hydroxy ocenol ether sulfonate(s) while the crude sulfonic acid is being introduced into the aqueous basic solution. A further embodiment of the process according to the invention concerns the addition of one or more hydroxy ocenol sulfonate(s) and/or hydroxy ocenol ether sulfonate(s) into the already combined mixture of crude sulfonic acid and aqueous basic solution, i.e. after the introduction of the crude sulfonic acid into the aqueous basic solution. What is preferred is an addition of one or more hydroxy ocenol sulfonate(s) or in mixtures with one or more hydroxy ocenol ether sulfonate(s) during the introduction of the crude sulfonic acid into the aqueous basic medium.

By the addition of the viscosity regulators from the group of hydroxy ocenol sulfonates or hydroxy ocenol ether sulfonates described in more detail above, the viscosity of highly concentrated ester sulfonate salt pastes is reduced in an advantageous way. Surprising here is not only the fact that even small quantities of added viscosity regulator are responsible for a reduction of the viscosity, but also that these quantities make possible a fall in the viscosity to values in the region of 10 to 90% of the viscosity value which the paste would have had without the addition of the viscosity regulators. It is therefore possible in the preferred embodiments of the process according to the invention to drastically reduce the viscosity, if one or more hydroxy ocenol sulfonates and/or hydroxy ocenol ether sulfonates are added to the reaction mixture in total quantities of 1 to 10 mol. percent. Advantageously the total quantity of the viscosity regulators named is in the region of 2 to 8 mol. percent. Such additives make possible a reduction of the viscosity both of highly concentrated, e.g. 60%, ester sulfonate salt pastes and lower percentage, e.g. 30%, ester sulfonate salt pastes to values which lie clearly below 50% of the viscosity value which the paste would have without the addition of the viscosity regulator.

The manufacture of the hydroxy ocenol sulfonates and hydroxy ocenol ether sulfonates used as viscosity regulators in the process according to the invention, is carried out in a manner described in co-pending U.S. patent application Ser. No. 226,596 which is now U.S. Pat. No. 4,8655,774 issued Sept. 12, 1989. In this process unsaturated fatty alcohols with 10 to 18 carbon atoms are alkoxylated with olefin epoxides, preferably ethylene oxide, propylene oxide and/or butylene oxide, and the products obtained are esterified with a carboxylic acid with 1 to 4 carbon atoms in the acyl radical. The unsaturate fatty alkenyl or fatty alkenyl polyoxyalkylene glycol esters obtained, which are predominantly manufactured from fats and/or oils of natural origin and contain as the fatty alkenyl radicals mainly oleyl groups, palmitoleyl groups, linoleyl groups, gadoleyl groups and/or erucyl groups, and possibly contain one or more alkylene glycol groups are then reacted with a sulfonation reagent, primarily sulfur trioxide. The reaction product is introduced into the aqueous solution of 1 to 2.5 mol. alkali metal-, alkaline earth metal - or ammonium hydroxide per mol. of added $SO_3$ and this solution is heated until there is hydrolysis of the ester and sultone groups obtained. In the process according to the invention such aqueous solutions are used in the most concentrated form possible. The hydroxy ocenol sulfonates or hydroxy ocenol ether sulfonates with sodium or ammonium groups on the sulfonate groups are preferably used. The quantities of the viscosity regulators used of 1 to 10 mol. percent, and particularly preferably 2 to 8 mol. percent, effect a clear reduction of the viscosity of the ester sulfonate salt pastes.

The invention is explained in more detail by the following examples.

In the following examples the viscosity of the ester sulfonate salt pastes is measured in an Epprecht-TV Viscometer or in a Brookfield-viscometer. The reduction of the viscosity by the addition according to the invention of viscosity regulators is not given in absolute numbers, because the viscosities (mPa.s) measured in the two viscometers are dependent on the rate of shear selected. Instead the viscosity value of the ester sulfonate salt pastes without viscosity regulators which is determined in each of the viscometers is set as "100% viscosity" and the relative reduction of the viscosity determined after the addition of the viscosity regulators. The measurements were repeated twice and the results averaged from all three measurements.

EXAMPLE 1

70 g (0.08 mol) of a 33% $C_{16/18}$ a $\alpha$-ester sulfonate paste free of di-salt and unsulfonated material was mixed with 18.4 g (0.008 mol., corresponding to a 10% addition) of a 36% hydroxy ocenol-lOEO-sulfonate-Na-salt paste (HOES 10-Na-salt) (I; X=OH; Y=$SO_3M$ with M=Na; (a+b+c)=14; Z=—$CH_2$—$CH_2O$—; x approx. 10; WAS (washing active substance)=0.277 mval/100g; US (unsulfonated material)=8%; $SO_4^{2-}$=2%; OAc$_-$=3%) and homogenized on the steam bath with intensive stirring.

In order to remove disturbing air bubbles, the homogenizate was centrifuged for 30 min. then brought to the measuring temperature of 45° C. in the steam bath and the viscosity was measured in an Epprecht-TV-viscometer (measuring body 2-4).

Viscosites measured

| | | |
|---|---|---|
| (a) | α-ester sulfonate (a-ES; Texin ES 68 of the Henkel Company), 33% | 7 620 mPa.s = 100% |
| (b) | α-ES + 10% by weight HOES10-Na-salt, 36% | 800 mPa.s = 11% |

EXAMPLE 2

70 g (0.14 mol.) of a 56% α-ester sulfonate paste free of di-salt and unsulfonated material was mixed with 8.9 g (0.007 mol., corresponding to an addition of 5 % by weight) of a 65% hydroxy ocenol-lOEO-sulfonate-Na-salt paste (I; X =OH; Y=$SO_3M$ with M=Na; (a+b+c)=14; Z=—$CH_2$—$CH_2O$—; x=approx. 10; WAS =0.53 mval/100g; US=12%; $SO_4^{2-}$=5%; OAc$^-$=4%) and homogenized on the steam-bath with intensive stirring.

In order to remove disturbing air bubbles the homogenizate was centrifuged for 30 min., then brought to the measuring temperature of 90° C. on the steam bath and the viscosity measured in a Brookfield viscometer (spindle 1, 60 r.p.m.).

Viscosities measured

| | | |
|---|---|---|
| (a) | α-ester sulfonate (a-Es; Texin ES 68 of the Henkel Company), 56% | 5 800 mPa.s = 100% |
| (b) | α-ES + 5% by weight (HOES10-Na-salt, 65% | 2 400 mPa.s = 41% |

COMPARATIVE EXAMPLE 1

In a blank test 70g (0.08 mol.) of a 33% α-ester sulfonate paste free of di-salt and unsulfonated material was added to 10% by weight of water and the viscosity determined according to Example 1.

Viscosities measured

| | |
|---|---|
| α-ester sulfonate (Texin ES 68), 33% | 7 620 mPa.s = 100% |
| α-ES + 10% by weight H$_2$O | 6 860 mPa.s = 90% |

COMPARATIVE EXAMPLE 2

In the method described in Comparative Example 1 the 33% α-ester sulfonate paste was added to 5 % by weight of water and the viscosity determined as in Example 1. The relative viscosity values measured can be seen from the following table.

EXAMPLE 3

Added to the α-sulfonate paste (33% AS) described in Example 1 in quantities of 5 and 10 % by weight was a hydroxy ocenol sulfonate of the general formula (I) (with X=OH; Y=SO$_3$M with M=Na; (a+b+c)=14) or 5% by weight of a hydroxy ocenol ether sulfate of the general formula (I) (with X=OH; Y=SO$_3$M with M=Na; Z=—CH$_2$— CH$_2$O—; (a+b+c)=14: x=approx. 10) and the viscosity determined in manner described in Example 1. The results can be seen from the following table.

EXAMPLE 4

In the manner described in Example 2, the 56% α-ester sulfonate paste given there was mixed with 5 or 10 % by weight of the hydroxy ocenol sulfonate (I) or with 10 % by weight of the hydroxy ocenol ether sulfonate (I), which was defined in Example 3. The relative viscosity was determined in the manner described in Example 2. The results can be taken from the following table.

COMPARATIVE EXAMPLES 3 and 4

In a further blank test 70 g (0.14 mol. of a 56% α-ester sulfonate paste free of disalt and unsulfonated material is mixed with 5 or 10 % by weight of water and the viscosity determined in the manner described in Example 2. The relative viscosities can also be taken from the following table.

TABLE

| Ex. | Texin ES68 AS (%) | Meth.[1] | HOS[2] weight % | HOES[3] weight % | H$_2$O weight % | Rel. Visc. % |
|---|---|---|---|---|---|---|
| 1a | 33 | A | — | — | — | 100 |
| 3a | 33 | A | 5 | — | — | 15 |
| 3b | 33 | A | 10 | — | — | 8 |
| 3c | 33 | A | — | 5 | — | 6 |
| 1b | 33 | A | — | 10 | — | 11 |
| Comp. 2 | 33 | A | — | — | 5 | 92 |
| Comp. 1 | 33 | A | — | — | 10 | 90 |
| 2a | 56 | B | — | — | — | 100 |
| 4a | 56 | B | 5 | — | — | 87 |
| 4b | 56 | B | 10 | — | — | 59 |
| 2b | 56 | B | — | 5 | — | 41 |
| 4c | 56 | B | — | 10 | — | 45 |
| Comp. 3 | 56 | B | — | — | 5 | 54 |
| Comp. 4 | 56 | B | — | — | 10 | 55 |

Notes:
[1]Method A:
Epprecht-TV-viscometer
45° C.
measuring body 2-4
Method B:
Brookfield viscometer
90° C.
spindle 1
60 r.p.m.
[2]HOS = hydroxy ocenol sulfonate I with X = OH;
Y = SO$_3$M with M = Na;
(a + b + c) = 14; x = o
[3]HOES10 = hydroxy ocenol ether sulfonate I with X = OH;
Y = SO$_3$M with M = Na;
Z = —CH$_2$CH$_2$O—;
(a + b + c) = 14;
x = approx. 10

EXAMPLE 5

200 g (0.88 mol.) of palm stearic acid methyl ester (IZ - 0.08, VZ=198.4, SZ=0.45, M=228.2) was placed in a 1-liter sulfonation reactor with a gas-inlet pipe and jacket cooling and reacted at 80° C. with 84 g (1.05 mol.) of SO$_3$, corresponding to a ratio of ester : SO$_3$=1:1.2.

The SO$_3$ was driven out from a corresponding amount of oleum by heating, diluted with nitrogen to a concentration of 5% by volume and introduced over 26 min into the methyl ester, the temperature of the reaction mixture being held constantly below 90° C. by intensive cooling.

After the sulfonation the acidic reaction product was first tempered for 25 min at 80° C., then cooled to 15° C., mixed with 40g, corresponding to 8 % by weight of a 56% aqueous solution of hydroxy ocenol-l0EO-sulfonate-Na-salt and stirred into a solution of 44g (1.1 mol.) of NaOH in approx. 500 ml of water.

Following this 70 g of the paste (AS-content =40.4%) obtained in this way was homogenized by intensive stirring, centrifuged for 30 min to remove air bubbles, brought to the measurement temperature of 45° C. on the steam bath and the viscosity determined in an Epprecht-TV-viscometer (measuring body 3-4).

The comparison was made against a sample to which no had been added during the neutralization to reduce viscosity.

Viscosities measured

| (a) | α-ester sulfonate (α-ES, 40%) | 9480 mPa.s 100% |
|---|---|---|
| (b) | α-ES + 8% by weight HOES 10-Na-salt 36% | 1990 mPa.s 21% |

COMPARATIVE EXAMPLE 5

In a comparative experiment 70 g of the 40.4% paste was mixed with 8% by weight of water and the viscosities were determined in the manner described in Example 5:

Viscosities measured

| (a) | α-ES (40%) | 9480 mPa.s 100% |
|---|---|---|
| (b) | α-ES + 8% by weight H$_2$O | 6420 mPa.s 68% |

We claim:
1. A process for the preparation of an aqueous concentrate of an α-sulfonated fatty acid alkyl ester comprising the steps of: (a) sulfonating an alkyl fatty acid ester with a sulfonating agent to produce an α-sulfonated fatty acid alkyl ester; (b) adding to said α-sulfonated fatty acid alkyl ester from about 1 to about 10 mole percent of the total moles of said α-sulfonated fatty acid alkyl ester of at least one compound of the formula

$$CH_3-(CH_2)_a-\underset{X}{CH}-(CH_2)_b-\underset{Y}{CH}-(CH_2)_c-CH_2-O-Z_n-H \quad (I)$$

wherein in the compound of formula I X and Y are different and are OH or SO₃M wherein M is selected from the group consisting of hydrogen, an alkali metal ion, an alkaline earth metal ion, or NR₄ wherein R is hydrogen, an alkyl or hydroxy alkaly radical having from 1 to 4 carbon atoms; a and c are integers having a value of from 0 to 18; b is an integer having a value of from 0 to 2 such that the sum of a+b+c is from 12 to 18; Z is an oxyethylene, oxypropylene, or oxybutylene group; n is an integer having a value of from 0 to 30; and (c) neutralizing said α-sulfonated fatty acid alkyl ester with an aqueous alkaline solution.

2. The process of claim 1 wherein the amount of said compound of formula I in step (b) is from about 2 mole percent to about 8 mole percent of the total moles of α-sulfonated fatty acid alkyl ester.

3. The process of claim 1 wherein in the compound of formula I M is NH₄ or Na⁺.

4. The process of claim 3 wherein in the compound of formula I Z is an oxyethylene group and n is an integer having a value of from 0 to 10.

5. The process of claim 4 wherein in the compound of formula 1 a+b+c is from about 16 to about 18.

6. The process of claim 1 wherein steps (b) and (c) are performed simultaneously.

7. The process of claim 1 wherein said sulfonating reagent is selected from the group consisting of gaseous sulfur trioxide or chlorosulfonic acid.

8. A composition in concentrated aqueous form comprising an aqueous solution of a salt of an α-sulfonated fatty acid alkyl ester and at least one compound having the formula

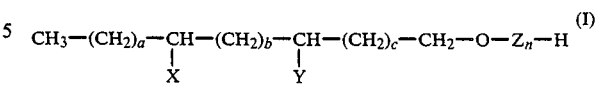

wherein X and Y are different and are OH or SO₃M wherein M is selected from the group consisting of hydrogen, an alkali metal ion, an alkaline earth metal ion, or NR₄ wherein R is hydrogen, an alkyl or hydroxy alkaly radical having from 1 to 4 carbon atoms; a and c are integers having a value of from 0 to 18; b is an integer having a value of from 0 to 2 such that the sum of a+b+c is from 12 to 18; Z is an oxyethylene, oxypropylene, or oxybutylene group; n is an integer having a value of from 0 to 30; wherein the amount of said compound having the formula (I) in said composition is from about 1 to about 10 mole percent of the total moles of said α-sulfonated fatty acid alkyl ester.

9. The composition claim 8 wherein M is NH₄ or Na⁺.

10. The composition of claim 9 wherein Z is an oxyethylene group and n is an integer having a value of from 0 to 10.

11. The composition of claim 9 wherein a+b+c is from about 16 to about 18.

* * * * *